United States Patent [19]

Colman et al.

[11] Patent Number: 5,047,323
[45] Date of Patent: Sep. 10, 1991

[54] METHOD FOR DETECTING HUMAN KININOGEN USING MONOCLONAL ANTIBODIES THERETO

[75] Inventors: Robert W. Colman; Alvin H. Schmaier, both of Philadelphia, Pa.

[73] Assignee: Temple University of the Commonwealth System of Higher Education, Philadelphia, Pa.

[21] Appl. No.: 429,262

[22] Filed: Oct. 30, 1989

Related U.S. Application Data

[62] Division of Ser. No. 821,367, Jan. 27, 1986, Pat. No. 4,908,431.

[51] Int. Cl.$^5$ .................. G01N 33/53; G01N 33/543
[52] U.S. Cl. ................................. 435/7.21; 436/518; 436/514; 436/533; 436/548; 435/7.24; 435/7.92; 435/7.93; 435/7.4
[58] Field of Search .................. 435/7; 436/518, 514, 436/515, 516, 533, 534, 548

[56] References Cited

PUBLICATIONS

Bedi, G. S. et al., "Single Step Purification of 'Kallikrein-Resistant' Kininogen from Rat Plasma Using Monoclonal-Antibody Immunoaffinity Chromatography", *Preparative Biochemistry*, 15(3): 159–169, 1985.

Schmaier, A. H. et al., "High-Molecular Weight Kininogen: A Secreted Platelet Protein", *J. Clin. Invest.*, 71: 1477–1489, 1983.

Goding, J. W., Monoclonal Antibodies: *Principles and Practice*, Academic Press, Inc., Orlando, 1983, pp. 56–97.

Berrettini, M. et al., "Immunological Studies of Human High Molecular Weight Kininogen (HMWK) Using Murine Monoclonal Antibodies (Mab)", *Thrombosis and Hemostasis*, 54(1): 229, Jul. 14, 1985.

Muller-Esterl et al., "Purification and Properties of Human Low Molecular Weight Kininogen", *Biochimica et Biophysica Acta*, 706, 145–152 (1982).

Kerbiriou et al., J. Biol. Chem., 255, 3952–3958 (1980).

*Primary Examiner*—Esther L. Kepplinger
*Assistant Examiner*—Laurie A. Scheiner
*Attorney, Agent, or Firm*—Seidel, Gonda, Lavorgna & Monaco

[57] ABSTRACT

Two novel cell lines, ATCC #HB-8963 and ATCC #HB-8964 produce monoclonal antibody to human kininogen. One of the antibodies specifically recognizes the heavy chain of high and low molecular weight kininogen (the later protein is identical to alpha cysteine protease inhibitor). The other antibody recognizes the light chain of high molecular weight kininogen. The hybridomas are formed by fusing spleen cells from immunized BALB/c AnSkh mice with P3X63Ag8 or SP2/0-Ag14 myeloma cells. Diagnostic, therapeutic and biochemical uses of the monoclonal antibodies are provided.

5 Claims, 5 Drawing Sheets

FIG. 3 — 2B5 IMMUNOBLOT OF KININOGENS
NHP | FITZ PLASMA | HMWK | HMWK COOMASIE

FIG. 7 — C11C1 MAB Immunoblot
NHP | FITZ | HMWK | HMWK (stained)

METHOD FOR DETECTING HUMAN KININOGEN USING MONOCLONAL ANTIBODIES THERETO

REFERENCE TO GOVERNMENT GRANT

The invention described herein was supported by National Institutes of Health grants HL00694 and HL24365. The United States Government has a royalty-free, nonexclusive and irrevocable license to practice the invention.

This is a divisional of application Ser. No. 06/821,367, filed Jan. 26, 1986, now U.S. Pat. No. 4,908,431.

FIELD OF THE INVENTION

This invention relates to hybrid cell lines for production of monoclonal antibodies to human kininogens, proteins which are found in nearly all human blood plasma, platelets, and kidney tissue. The invention also relates to the antibody produced by these cell lines, and to diagnostic, therapeutic and biochemical methods and compositions using the same.

BACKGROUND OF THE INVENTION

The plasma kininogens are single-chain glycoproteins which are present in human blood plasma and tissues in two forms: high molecular weight kininogen (120 kDa) and low molecular weight kininogen (64 kDa). The gene that controls the synthesis of both kininogens is the same (Kitamura, N. et al, Nature 305, 545, 1983). The difference between the high molecular weight form and the low molecular weight form is the addition of an unique light chain by a posttranscriptional modification on each of the molecules. The presence of a 56 kDa light chain on high molecular weight kininogen gives this form of kininogen unique antigenic as well as functional properties. The plasma concentration of high molecular weight kininogen is 0.67 micromolar, while the concentration of low molecular weight kininogen is 2.4 micromolar.

The functions of the plasma kininogens are as follows. Both high molecular weight and low molecular weight kininogen are parent molecules for the decapeptide, bradykinin, the most potent naturally-occurring vasodilitory substance. Bradykinin is best liberated from high molecular weight kininogen by plasma kallikrein, but low molecular weight kininogen is a better substrate for tissue kallikreins to release bradykinin.

High molecular weight kininogen also functions as a cofactor for the activation of the following plasma zymogens: factor XII, prekallikrein, and factor XI. These three plasma zymogens/enzymes, along with high molecular weight kininogen, comprise the proteins of the contact phase of plasma proteolysis. In addition to being a cofactor for activation of each of these plasma zymogens, high molecular weight kininogen is also a substrate of each of their proteolytic forms. Moreover, high molecular weight kininogen serves to order the activation and inhibition of these proteases since 75% of plasma prekallikrein and 90% of plasma factor XI circulate in plasma in complex with high molecular weight kininogen. The proteins of the contact phase of plasma proteolysis are a group of proteins that link the plasma proteolytic systems of coagulation, fibrinolysis, complement activation, and blood pressure control.

Low molecular weight kininogen, the preferred substrate for the tissue kallikreins, has recently been identified as being identical to alpha cysteine protease inhibitor—a major plasma inhibitor of cysteine proteases (Ohkubo, I. et al, Biochem. 23, 3891, 1984). Since the heavy chain of both high molecular weight and low molecular weight kininogen are identical, high molecular weight kininogen has also been shown to inhibit cysteine proteases (Muller-Esterl, W., FEBS 182, 310, 1985; Sueyoshi, T. et al, FEBS 182, 193, 1985). High molecular weight kininogen has been shown in our laboratories to be the most potent inhibitor of the calcium-activated cysteine protease from platelets (Schmaier, A. H. et al, Blood 66 (Suppl):313A, 1985).

Using high molecular weight kininogen as an example, the molecular structure of the kininogen molecules, as the structure relates to the function of the molecule, can be described. When the intact 120 kDa high molecular weight kininogen molecule is cleaved by plasma kallikrein, the initial two cleavages results in the liberation of the 1000 molecular weight peptide bradykinin, leaving a residual twochain molecule joined together by disulfide bonds. A residual heavy chain (64 kDa) is identical to the heavy chain of plasma low molecular weight kininogen (alpha cysteine protease inhibitor) which can function as a cysteine protease inhibitor. Likewise, an intermediate 56 kDa light chain is formed which contains the unique antigenic and functional properties of the high molecular weight kininogen molecule. This light chain serves as the site for the surface-mediated activities of the molecule that are involved in activating and regulating inhibition of the contact phase zymogens: factor XII, prekallikrein and factor XI. Further cleavage of the 56 kDa light chain of high molecular weight kininogen by kallikrein results in a stable 46 kDa light chain with similar functional properties.

It is hypothesized, but not yet conclusively shown, that the role of plasma kininogens as cysteine protease inhibitors limits the extent of tissue injury upon cytolytic destruction of cells by cysteine proteases. This type of injury occurs as result of complement activation and mechanical destruction. Purified plasma kininogen could be used as a therapeutic tool in the treatment of such conditions as peridontal disease and intervertebral disc disease, where cysteine proteases are pathogenic in these disorders.

The surface-mediated activation of the proteins of the contact phase of plasma proteolysis (factors XI and XII; prekallikrein; high molecular weight kininogen) occurs in pathologic states. Gram negative sepsis, typhoid fever, and acute attacks of hereditary angioedema are serious disease states wherein these proteins are altered and the contact activation system is activated. Early detection of activation of the contact system proteins could have prognostic and therapeutic results on the outcome of treating the above conditions. The ability to develop means for early detection of activation of the contact system proteins can be developed by use of antigenic assays to activation fragments of these proteins.

Kohler and Milstein (Nature 256, 493–497, 1975) were the first to describe the fusion of myeloma cells to immune spleen cells from mice to generate continuous cell lines. These hybrid cell lines, or hybridomas, have characteristics that neither the parental myeloma cells nor parental immune spleen cell possess. Hybridomas are capable of continuously producing homogeneous (monoclonal) antibodies. Prior to the work of Kohler and Milstein, only polyclonal antisera could be obtained.

Although techniques for the production of hybridomas are now extensively described in the literature, e.g., *Monoclonal Antibodies, Hybridomas: A New Dimension In Biological Analysis*, R. H. Kennet, T. J. McKearn, and K. B. Bechtol, eds., Plenum Press, New York and London (1980), there is no general method for obtaining successful monoclonal antibody-producing hybridomas which can be used with all antigens. Fusion techniques must be varied in each case to obtain hybridomas producing monoclonal antibody to the desired antigen. In order to obtain antibodies specific to a single antigen, laborious purification techniques are required to provide highly purified antigen for immunization. The production of monoclonal antibodies for any given antigen is still a highly empirical process.

The kininogens have been detected in blood by means of coagulant and immunochemical assays using polyclonal antisera. There have been no reports of monoclonal antibodies against kininogens prior to the present invention. The dearth of literature accounts of monoclonal antibodies to the kininogens is no doubt due to difficulties in the purification of antigen and/or the lack of success in preparation of suitable hybridomas.

Hereinafter, "human kininogen", shall mean, unless otherwise indicated, both the high and low molecular weight forms of any kininogen molecule, in all its various forms derived from human plasma, platelets, kidney, skin, leukocytes or other tissues or organs, regardless of whether found in the fluid or the tissue phase.

"HMWK" shall mean high molecular weight human kininogen.

"LMWK" shall mean low molecular weight human kininogen, also known as alpha cysteine protease inhibitor, or alphalthiol protease inhibitor, or $alpha_2$-thiol protease inhibitor.

"Heavy chain" shall mean, when referring or relating to human kininogen, the 64 kDa kallikrein-cleavage fragment of HMWK, said fragment being identical to the heavy chain of LMWK.

"Light chain" shall mean, when referring or relating to human kininogen, the 56 kDa intermediate kallikrein-cleavage fragment of HMWK which has the ability to correct the coagulant defect in total kininogen-deficient plasma.

SUMMARY OF THE INVENTION

According to the present invention, novel hybridomas have been prepared providing cell lines producing monoclonal antibodies which specifically bind to an antigenic determinant of human kininogen. Each hybridoma comprises a cell hybrid formed by fusion of cells from a myeloma line and spleen cells from a donor previously immunized with human kininogen. The hybridomas are, respectively, ATCC #HB-8963 and #HB-8964. Each antibody so produced is specific for an antigenic determinant of human kininogen. The purified monoclonal antibody contains essentially no other anti-human immunoglobulin. The hybridomas may be cultured in vitro to secrete antibodies.

The hybrid cell lines of the present invention may be prepared by first immunizing mice with purified human kininogen. The spleen cells are then removed and a suspension thereof is made. The spleen cells are fused with mouse myeloma cells in the presence of a fusion promotor. The fused cells are diluted and cultured in separate wells in a medium which will not support the unfused myeloma cells. The supernatant in each well is assayed for the presence of antibody to human kininogen by an enzyme-linked immunosorbent assay (ELISA). Hybridomas secreting antibody which binds to human kininogen are selected and cloned.

The hybridomas are cultured in a suitable medium and the antibody is recovered from the supernatant. Alternatively, the clones are transferred intraperitoneally into mice, and the resulting malignant ascites and serum containing the desired antibody are harvested.

A method for detecting the level of human kininogen in specimens of interest is provided. A monoclonal antibody according to the present invention, which binds to an antigenic determinant of human kininogen, is contacted with the specimen under conditions such that an immune complex forms between the monoclonal antibody and any kininogen in the specimen. The material bound by the antibody is measured by standard assay means. The invention is particularly useful for detecting variations in the level of plasma kininogens in human plasma.

The antibodies of the invention may be bound to an immobilized matrix and used to purify either HMWK or LMWK. Matrices of this type charged with HMWK may be used to purify prekallikrein and factor XI, which bind to HMWK.

The subject hybridomas are identified herein by the same number assigned to the antibody produced thereby. Thus, for example, the designation "2B5" pertains to both the hybridoma 2B5-G4-F4 and the monoclonal antibody produced by this hybridoma. The particular material referred to, that is, hybridoma versus antibody, is apparent from the context.

The subject hybridomas were deposited in the American Type Culture Collection, 12301 Parklawn Drive, Rockville, Md. 20852, and were given the following ATCC accession numbers: #HB-8963 for 2B5-G4-F4; #HB-8964 for C11C1. The hybridomas were deposited on December 6, 1985.

BRIEF DESCRIPTION OF THE FIGURES

FIG. 7 is an immunoblot generated with the CllCl antibody from the alkaline polyacrylamide gel electrophoresis of (from left to right) (i) kininogen antigen from normal plasma ("NHP"), (ii) kininogen antigen from HMWK-deficient plasma ("FITZ"), (iii) purified HMWK ("HMWK"), and (iv) purified HMWK detected by staining with Coomasie blue ("HMWK (stained)").

DETAILED DESCRIPTION OF THE INVENTION

Figure 1:
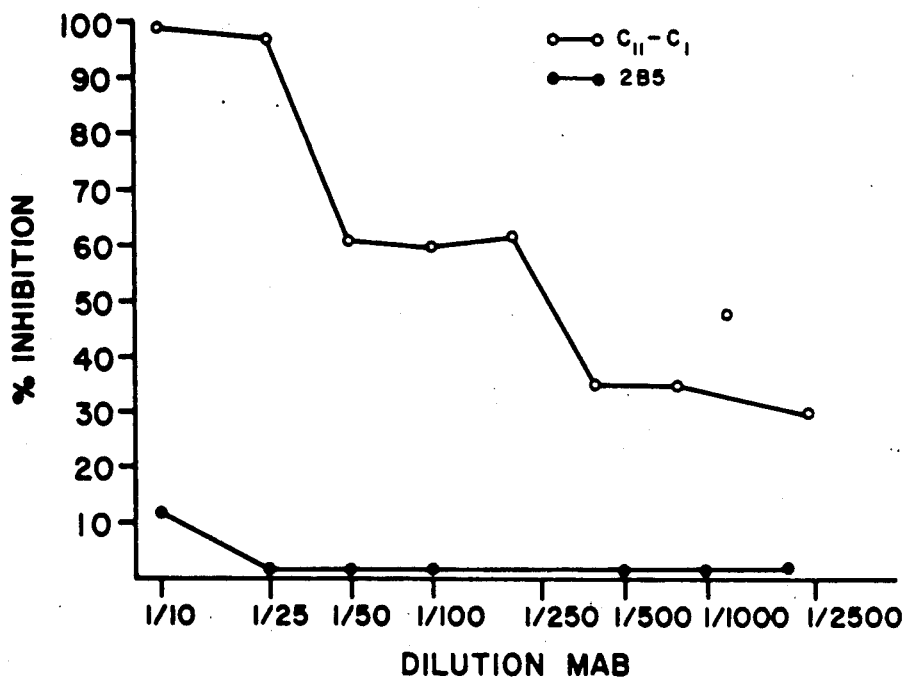
FIG. 1 is a plot of the neutralization of HMWK coagulant activity by the 2B5 and C11C1 antibodies. Percent inhibition of HMWK coagulant activity (ordinate) is plotted against antibody dilution (abscissa). The (○) curve represents inhibition produced by the C11C1 antibody; the (●) curve is inhibition by the 2B5 antibody.

The cell hybrids of the present invention produce monoclonal antibodies that react with human plasma kininogen. The monoclonal antibody 2B5 reacts with kininogen antigen in normal plasma with two bands, kininogen antigen in HMWK deficient plasma, and purified alkylated and reduced HMWK heavy chain. In addition, 2B5 does not neutralize HMWK coagulant activity in plasma. These combined studies indicate that the 2B5 monoclonal antibody is directed to the HMWK heavy chain, which is the same as the heavy chain of LMWK. The monoclonal antibody CllCl reacts with kininogen antigen (one band) in normal plasma but not with kininogen antigen in HMWK deficient plasma. The CllCl antibody also recognizes kininogen antigen in human platelets and neutralizes the coagulant activity of HMWK. These combined studies indicate that the CllCl antibody is directed to the HMWK light chain. Both monoclonal antibodies produced from the cell hybrids make antibodies of the subclass IgG$_1$, kappa light chain. The purified antibodies have a molecular weight on non-reduced 8% sodium dodecyl sulfate polyacrylamide gels of 200 kDa, which upon reduction yields 50 kDa and 28 kDa fragments. The antibodies are conformationally specific since they do not recognize kininogen antigen that has been treated with sodium dodecyl sulfate.

HMWK is purified from plasma by a method that relies on the difference between isoelectric points, and therefore differences in dissociation constants, between HMWK and other plasma proteins. This procedure, which consists of quarternary ethyl aminoethyl Sephadex (QAE) chromatography, ammonium sulfate precipitation, and sulfopropyl (SP) chromatography, results in a purified protein with greater than 98% homogeneity as determined by sodium dodecyl sulfate polyacrylamide gel electrophoresis (SDS-PAGE). Other purification methods may be used, including binding with immobilized monoclonal antibodies according to the present invention.

Mice are immunized with purified HMWK from plasma. BALB/c AnSkh mice are preferred, although other strains may be used. The immunization schedule and concentration of antigen administered should be such so as to produce useful quantities of suitably primed splenocytes.

Upon completion of the immunization regimen, more fully described below, the mice are sacrificed and their spleens removed. A suspension of splenocytes in a suitable dium is prepared. Approximately 2.5–5 ml of medium per spleen is sufficient. The protocols for in vitro cell suspension are well established.

The spleen cells are fused with mouse myeloma cells by means of a fusion promoter. The preferred fusion promoter is polyetheylene glycol, molecular weight 1,300–1,600. Other promoters may be used. The mouse myeloma cell line is preferably one of the "drug-resistant" types, to enable selection of hybrids. The most frequently used class of myelomas are the 8-azaguanine-resistant cell lines, which are widely known and available. These cell lines lack the enzyme hypoxanthine guanine phosphoribosyl transferase and therefore do not survive in "HAT" (hypoxanthine-aminopterin-thymidine) medium. The use of myeloma cells with different genetic deficiencies (e.g., other enzyme deficiencies, drug sensitivities, etc.) that can be selected against in medium supporting the growth of genotypically competent hybrids is also possible. Additionally, it is suggested that the myeloma cell line should not itself produce any antibody, although in some circumstances, such as in the production of the CllCl antibody, secreting myeloma cell lines can be used.

While the preferred fusion promoter is polyethylene glycol of average molecular weight 1,300–1,600 (available from ATCC), other known fusion promoters may be used.

Fusion of cells may be carried out in an adherent monolayer, such as according to the method described by T. J. McKearn in "Fusion of Cells in an Adherent Monolayer" *Monoclonal Antibodies: Hybridomas: A New Dimension In Biological Analysis*, (Kennett, R. H., McKearn, T. J., and Bechtol, K. B., eds., Plenum Press, New York and London, 368–369, 1980). Other fusion techniques may be employed A cell ratio of 2–5:1 spleen cells per myeloma cell may be used. This ratio may be varied depending on the source of spleen or myeloma cells.

A mixture of unfused myeloma cells, unfused spleen cells and fused cells are distributed for culturing in separate compartments (e.g., the wells of microtiter plates) in a selective medium in which the unfused myeloma cells will not survive. Distribution of the cells may be by resuspension in a volume of diluent which is statistically calculated to isolate a desired number of cells per compartment. See, McKearn, T. J., "Cloning of Hybridoma Cell Lines by Limiting Dilution in Fluid Phase" in *Monoclonal Antibodies*, p. 374.

When HAT is used as the medium, unfused 8-azaguanineresistant myeloma cells will not grow. Unfused spleen cells will normally die after a few days, since they are non-malignant. Culturing proceeds for a time sufficient to allow their death. Fused cells continue to reproduce and grow in the selective medium.

The supernatant in each container or compartment having hybrid cell growth is screened and evaluated for the presence of antibody to human kininogen. Any suitable antibody-binding detection method may be used, e.g., enzymelinked immunosorbent assay, radioimmunoassay, etc.

After selection and cloning, monoclonal antibody to human kininogen may be produced by in vitro culturing of the hybridomas or by in vivo peritoneal exudate induction in mice. The first method will yield monoclonal antibody of higher purity. The antibody is recovered from the supernatant essentially free of undersired immunoglobulin. Antibody concentrations of 25-50 micrograms/ml are possible by this method. In growth media containing serum (such as fetal calf serum) a small amount of other immunoglobulin is present.

Where concentrations of antibody larger than those obtained by in vitro culturing of hybridomas are required, the subject hybridomas may be injected into the peritoneal cavity of syngeneic or semisyngeneic mice. After a suitable period of incubation, the hybridomas cause formation of antibody-secreting tumors, which will produce 4-10 mg of antibody per ml of peritoneal exudate of the injected mouse. Since mice have normal antibodies in their blood and ascites, a contamination of about 5% from the host mouse in inevitable. Purification of ascites monoclonal antibody may remove these contaminants. The resultant antibody is of high titer, being active at dilutions of 1:300,000 or higher.

The following procedure is illustrative of methods for purifying HMWK immunogen for use in preparing hybrid cell lines according to the present invention.

I. Preparation Of The Immunogen

HMWK is purified according to the procedure of Kerbirious and Griffin, J. Biol. Chem. 254, 12020 (1979) as follows, with modifications. All operations are carried out in plastic material since glass activates the coagulation system. All reagents are purchased from Sigma Chemical Co. 0.1 M epsilon aminocaproic acid (EACA) is added to all buffers.

Four hundred fifty ml of blood from two donors are freshly collected into 50 ml of 3.8 g % (i.e., g/dl) sodium citrate containing 37.5 mg soybean trypsin inhibitor (SBTI)/50 ml, 150 mg polybrene/50 ml, 10 mM EDTA, 10 mM benzamidine and 0.02% $NaN_3$. Platelet-poor plasma is prepared by centrifugation at 1,000 $X_g$ for 30 min at 23° C. Diisopropylfluorophosphate (DFP) (2 mM final concentration) is added to the platelet-poor plasma before the purification. (DFP is also added to pooled material containing HMWK after the ammonium sulfate precipitation described below and prior to chromatography on SP Sephadex). Once the plasma is incubated for 30 min with DFP, it is then diluted 2:3 with 0.03 M Tris Cl, 3 mM benzamidine, 3 mM EDTA, 0.06% $NaN_3$ and 0.3 M EACA, pH 8.0. The plasma is then absorbed in a batch fashion on QAE Sephadex. The gel is equilibrated with 0.01 M Tris, 1 mM benzamidine, 1 mM EDTA, 0.1 M EACA, pH 8.0 containing 50 microgram/ml polybrene (4-6 mohm). After the plasma is applied, the column is washed with 0.121 M Tris, 0.044 M succinic acid, 0.103 M NaCl, 1 mM EDTA, 1 mM benzamidine, 0.02% $NaN_3$ and 0.1 M EACA, pH 7.7 (14-15 mohm) until the absorbance at 280 nm is less than 0.1. HMWK is eluted from the anion exchanger with 0.199 M Tris, 0.075 M succinic acid, 0.182 M NaCl, 1 mM EDTA, 1 mM benzamidine, 0.02% $NaN_3$ and 0.1 M EACA, pH 7.4 (23-25 mohm). After 50% ammonium sulfate precipitation and dialysis of the resuspended precipitate against 0.05 M sodium acetate, 0.075 M NaCl, 1 mM EDTA, 1 mM benzamidine, 0.02% $NaN_3$ and 0.1 M EACA, pH 5.3 (7-9 mohms), the HMWK is applied to a SP Sephadex column equilibrated in the same buffer. After washing the column, a linear gradient is applied with 0.1 M sodium acetate, 0.15 M NaCl, 1 mM EDTA, 1 mM benzamidine, 0.02% $NaN_3$ and 0.1 M EACA, pH 5.3 (15-18 mohm) in the proximal chamber and the same buffer containing 0.5 M NaCl (32-38 mohms) in the distal chamber. The HMWK elutes after 1½ to 2 column volumes has passed from the gradient.

The following are two typical procedures for preparing hybrid cell lines according to the present invention, which is not intended to be limited to the same.

II. Preparation Of The C11Cl Monoclonal Antibody

A. Immunization

Four male BALB/c AnSkh mice, 6 weeks old (Temple University, Skin and Cancer Hospital) are immunized intraperitoneally with 100 micrograms of sterile protein/mouse in complete Freund's adjuvant (week 0) and then again intraperitoneally with 200 micrograms of protein/mouse at week one. At week two, a third 100 microgram injection in 0.1 ml incomplete Freund's adjuvant is given. At week three, a fourth intraperitoneal injection with 200 micrograms of antigen is given. Four days later, the spleens from two of these mice are removed aseptically and placed in petri dishes containing 5 ml of RPMI-Versene (65 ml RPMI plus 35 ml versene stock—8.0 gm NaCl, 0.2 gm KCl, 2.1 gm $Na_2HPO_4 \cdot 7H_2O$, 0.2 gm $KH_2PO_4$, 1.0 gm EDTA in 1 liter $H_2O$, pH 7.2). Using two syringes with sterile bent needles, the spleens are teased apart into a suspension. The suspension is transferred to a 15 ml sterile conical tube and allowed to sit for 1 min. After the large debris settles, the cell-suspension is transferred into another centrifuge tube. Two ml of fetal calf serum is gently added to the bottom of the tube to form a gradient, and the entire contents of the tube are centrifuged at 1000 RPM for 8 minutes. After discarding the supernatant, the cells are resuspended in 2 ml of ice cold 0.83 M $NH_4Cl$ for 1 minute in order to lyse red blood cells. The cell suspension is diluted in 8 ml of 85% MEM (modified Eagle's Medium) plus 15% fetal calf serum. After making another 2 ml fetal calf serum gradient on the bottom of the tube, the entire contents are centrifuged at 1000 RPM for 8 minutes. The supernatant is removed and the cells are washed by gentle centrifugation at 1000 RPM for 8 minutes after resuspension in 10 ml RPMI-Versene. P3X63Ag8 secretor myeloma cells used in the hybridization procedure are washed in the same way as the unlysed splenocytes.

B. Preparation of Splenocyte Feeder Layers

On the day of fusion, 1 ml of immune splenocytes from the 10 ml RPMI-Versene suspension of the splenocytes is removed to be used for feeder layers. The cells are placed into a separate tube containing 5 ml of MEM +HAT +15% fetal calf serum.

C. Hybridization

Fusion is carried out as follows. After centrifugation of the myeloma cells and splenocytes, 5 ml of RPMI-Versene is added to each tube. The contents of one tube are combined with the other. The ratio of spleen to myeloma cells is 5:1. After combining the cells, they are washed twice by centrifugation with RPMI-Versene. Fusion is performed by adding 1 ml of solution of PEG 1450 (38%)—RPMI-Versens (62%), pH 7.8 warmed to 37°. The cell pellet is resuspended by gently tapping the tube. After 1 min, 1 ml of RPMI-Versene is added. After an additional 2 min wait, 2 ml of RPMI-Versene is added. After an additional 5 min, 5 ml of DME (Dulbeco's Modified Eagle's Medium, Gilbco, Grand Island, N.Y.) +10% fetal calf serum is added. The cell suspension is then centrifuged at 800 RPM for 8 min, and after the supernatant is removed, the cells are resuspended in 10 ml of DME +10% fetal calf serum +1 ml RPMI-Versene. This tube, along with a tube containing the feeder layer cells, is incubated at 5% $CO_2$ for 45 min. After the incubation, 0.1 ml aliquots of the hybrid cell suspension are plated onto 24-well Linbro cluster plates with each well containing 2 ml of DME +HAT. An aliquot of the feeder layer cells is also placed into each well. The plates are incubated overnight at 37° with a 5% $CO_2$ humid atmosphere.

D. Selection and Growth Of Hybridoma

Following overnight incubation, half the volume of each of the wells on the 24-well plate is removed and 1 ml of fresh DME +HAT is added. The cells are allowed to grow without change in the medium. The hybrids were screened daily and on day ten after hybridization the first colony growth is noted. Colony growth is maintained in DME +HAT +10% fetal calf serum. Hybridoma colonies with antibody reactive to the immunogen are selected and cloned by limiting dilution techniques. Cloning of the hybridomas is performed according to the procedure of McKearn, T. J. "Cloning of Hybridoma Cells by Limiting Dilution and Fluid Phase" in *Monoclonal Antibodies*, p. 374 in 80% (DME+15% fetal calf serum +HT), 20% conditioned media. Conditioned media is prepared by growing the myeloma cell line in DME+10% fetal calf serum and collecting the supernatant.

Cells from the hardiest clone were grown in culture and the supernatant was harvested. This culture supernatant was designated CllCl. The antibody was characterized by studies on the culture supernatant, as well as by studies on purified antibody using (i) pure immunogen, (ii) unique plasmas, (iii) ELISA and (iv) competitive ELISA (CELISA).

III. Preparation Of The 2B5 Monoclonal Antibody

A. Immunization

Four male or female BALB/c AnSkh mice, 8-10 weeks old (Temple University, Skin and Cancer Hospital) are immunized subcutaneously with 50 micrograms of protein/mouse in complete Freund's adjuvant (week 0) and then again subcutaneously with 50 micrograms of protein/mouse in incomplete Freund's adjuvant at week 5. Blood is removed and screened at week 7 for antibodies to the immunogen using emzyme-linked immunosorbent assay. At week 11, 50 micrograms of immunogen/mouse in 0.15 M sodium chloride are intraperitoneally injected. Four days later, blood is removed from the retroorbital plexus of each mouse under light anesthesia, and the two strongest positive mice are selected as spleen donors. The spleens of these animals are asceptically removed and placed in tissue cultured dishes (15×60 mm) containing Hank's balanced salt solution ("HBSS", Gibco) to which 50 micrograms/ml of gentamycin or "PEN/STREP" (Gibco) are added. The latter is a mixture of penicillin and streptomycin. The spleens are then transferred into other culture dishes containing HBSS. The spleens are teased apart with sterile forceps and then transferred into a centrifuge tube which is placed in ice for two minutes to allow large debris to settle. The cell suspension is transferred into another centrifuge tube and spun for 10 minutes at 1,200 rpm. After discarding the supernatant, the cells are resuspended in 5-10 ml of 0.17 M $NH_4Cl$ (ice cold) and placed in ice for 5 minutes with occasional mixing in order to lyse red blood cells. The cell suspension is gently underlaid into 10 ml of 1:1 dilution of HBSS:normal serum and centrifuged at 1,200 rpm for 10 minutes. Fetal calf serum ("FCS") may be used as the normal serum. The cells are then washed thrice in DME. The number and variability of cells is then determined.

SP2/O-Ag14 myeloma cells used in the hybridization procedure are washed in the same way as the unlysed splenocytes.

B. Preparation Of Splenocyte Feeder Layers

On the day of fusion, non-immune splenocytes from the same mouse strain as immunized above are processed according to the same procedure without immunization and without washing in DME. These non-immune splenocytes are used to prepare feeder layers as follows. The non-immune cells are resuspended in DME+HAT+20% FCS to a density of 2-4 ×$10^6$ cells/ml. These cells are seeded onto 96-well plates (1-2×$10^5$ cells/well) and incubated in 5% $CO_2$ at 37° C. overnight as a sterility check for plating out hybrid cells.

C. Hybridization

Fusion is carried out as follows. 1.5 ml of immune splenocytes and 1.5 ml of SP2/O-Ag14 are pipetted onto a Concanavalin A-coated plate. The cell concentration of each cell type is adjusted so that the ratio of splenocytes to SP2/O cells is 2-3:1, with a total of 7-10×$10^7$ cells/plate. The plates are then incubated in 5% $CO_2$ at 37° C. for 45-60 minutes to allow for attachment of the cells to Concanavalin A. Fusion is performed by adding 1 ml of a 50% DME:PEG solution to each plate, drop by drop. The plates are left standing for 15 seconds after the addition of the first drop. The cells are then washed twice with 5 ml of DME. Following addition of 5 ml of DME +20% FCS/plate, the cells are incubated overnight.

D. Selection And Growth Of Hybridomas

Following overnight incubation, the cells from the above hybridization procedure are transferred into centrifuge tubes and spun at 1,500 rpm for 15 minutes. The supernatants are discarded. The cells from each tube are suspended in 40-45 ml of DME +HAT +20% FCS and transferred into the 96-well plates (0.1 ml cell/well) containing non-immune splenocyte feeder layers as prepared above. The plates are cultured with 10% $CO_2$ at 37° C. in a humid atmosphere. The cells are allowed to grow for 3-5 days, after which an additional 0.1 ml of DME +HAT +20% FCS are added to each well. Hybrids are checked daily. Three to four weeks after fusion, the cells are switched to DME +HAT +10% FCS (no aminopterin). Hybridoma cultures with antibody reactive to the immunogen are selected and cloned by a limiting dilution technique.

Cells from the strongest positive culture, designated 2B5, were injected intraperitoneally (about $2\times 10^6$ cells in 0.5 ml PBS/mouse) into four BALB/c mice which are primed 10-14 days previously with 0.5 ml of pristane (2,6,10,14-tetramethylpentadecane). After 7-14 days, the blood was removed from the retro-orbital plexus of each mouse under light ether anesthesia and the tumor-induced ascites fluid was harvested. The antibody titer of 2B5 was determined in the ascites fluid using pure immunogen and ELISA. The antibody was characterized by studies on ascites as well as by studies on purified antibody using (i) pure immunogen, (ii) unique plasmas, (iii) ELISA, and (iv) competitive ELISA ("CELISA").

IV. Purification Of C11C1 and 2B5 Antibody

Antibody from culture supernatant and ascites fluid prepared above are purified as follows. Antibody in the culture fluid is initially concentrated using ammonium sulfate. One hundred ml of culture fluid is subjected to two successive 50% ammonium sulfate precipitations following by overnight dialysis against 0.01 M Tris Cl, 0.15 M NaCl, pH 7.4 (TBS). After dialysis, the material is concentrated to 1 to 2 ml. Concentrated culture supernatant antibody or ascites is then diluted 1:1 in the binding buffer for a modified Protein A affinity chromatography system (Affi-Gel Protein A, Bio Rad Corp., Richmond, Calif.). After slowly applying the crude material to the Protein A column and then washing the column with binding buffer such that the absorbance at 280 nm is less than 0.025, the antibody is eluted with an acidic buffer. The peak of elution is pooled and immediately dialysed against TBS. Final antibody is concentrated to 2 to 5 mg/ml. The quality of the purification is monitored by determining the residual amount of antibody that does not bind to the column or does not elute from the column by performing direct binding ELISA on the chromatography wash and regeneration material. The purity of the final antibody preparation is determined by sodium dodecyl sulfate polyacrylamide gel electrophoresis according to the procedure of Laemmli, Nature 227, 680 (1970).

V. Characterization Of The Monoclonal Antibodies

The two monoclonal antibodies of the present invention reacted with biochemically pure plasma HMWK by direct-binding ELISA. Studies were instituted to determine which portion(s) of the HMWK molecule these antibodies were directed toward.

Initial studies were performed to determine whether either of the monoclonal antibodies neutralized HMWK coagulant activity. Each purified antibody was first tested to determine if it had any coagulant activity itself. Neither purified antibody had any intrinsic coagulant activity. Normal plasma was diluted and then incubated with decreasing dilutions of purified monoclonal antibodies (from 1:10 to 1:2500) overnight at 4°. The next day the ability of this antibody-treated normal plasma to correct the coagulant activity of total kininogen-deficient plasma was tested (FIG. 1). As can be seen in the figure, the C11C1 antibody at the lower dilution completely inhibited the coagulant activity of normal plasma whereas the 2B5 antibody did not. These findings suggest that the C11C1 antibody is directed to the light chain of HMWK—that portion of the molecule which contains the coagulant portion—or to a site on the heavy chain adjacent to the light chain which can sterically interfere with the latter's function. The 2B5 antibody, which did not neutralize the coagulant function of the HMWK molecule, must be directed to the heavy chain or a portion on the light chain of HMWK not involved with coagulant function. In order to clarify what segment of the kininogen molecule these monoclonal antibodies were directed toward, various immunochemical studies were performed.

Figure 2:
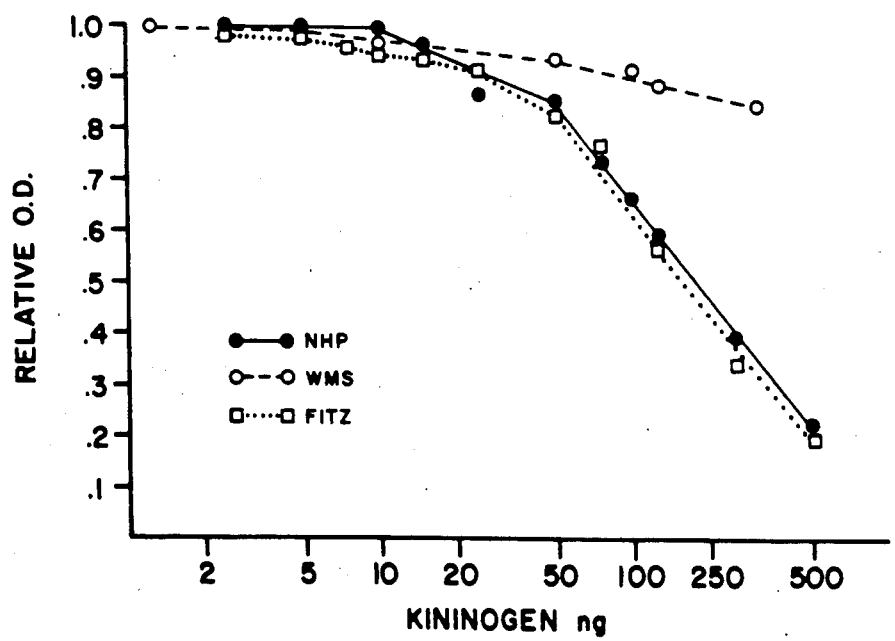
FIG. 2 is a plot of the competition inhibition of the 2B5 antibody produced by normal plasma (○ . . . ○), HMWK deficient plasma (□ . . . □), and total kininogen deficient plasma (○ . . . ○).

Initial immunochemical studies utilized a competitive enzyme-linked immunochemical assay (CELISA) developed by Schmaier et al, J. Clin. Invest. 71, 1477 (1983). Since nature has provided genetic variant plasmas which have either an absence of HMWK or total kininogen (both high and low molecular weight kininogen) the ability of each of these plasmas to consume the monoclonal antibodies was tested. As shown in FIG. 2, both normal plasma and HMWK-deficient plasma (Fitzgerald Plasma), but not total kininogen-deficient plasma (Williams Plasma), decreased the titer of the 2B5 antibody. This finding suggests that the 2B5 antibody is directed to the portion of the HMWK molecule common to both normal and HMWK-deficient plasma. Since the latter plasma contains 40% normal LMWK levels, and since the LMWK heavy chain is identical to the HMWK heavy chain, the 2B5 antibody must be directed to the HMWK heavy chain.

Figure 3:
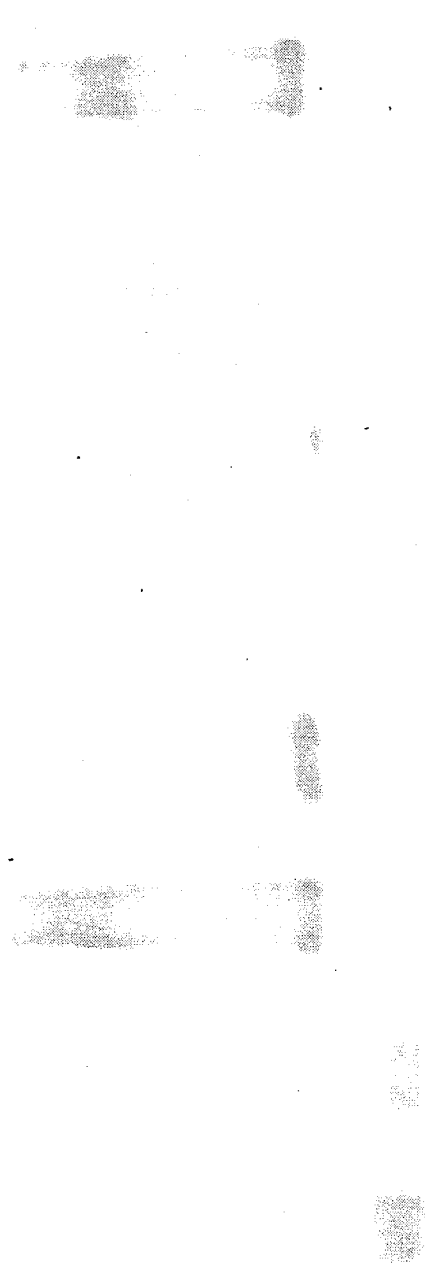
FIG. 3 is an immunoblot generated with the 2B5 antibody from the alkaline polyacrylamide gel electrophoresis of (from left to right) (i) kininogen antigen in normal plasma ("NHP"), (ii) kininogen antigen in HMWK-deficient plasma ("FITZ PLASMA"), (iii) purified HMWK ("HMWK") and (iv) purified HMWK detected by Coomasie blue staining ("HMWK COOMASIE").

The specificity of the 2B5 antibody for the HMWK heavy chain was further tested by immunoblot studies (FIG. 3). Initial studies using a direct binding ELISA and immunoblot showed that the 2B5 antibody was a conformationally specific antibody since it did not recognize HMWK antigen that had been treated with sodium dodecyl sulfate. An 8% alkaline polyacrylamide gel electrophoresis system was used to perform the immunoblot studies (Davis, B. J., Ann. N.Y. Acad. Sci. 121, 404, 1964). Purified HMWK, HMWK-deficient plasma, and normal plasma were applied to the alkaline gel and electrobloted onto nitrocellulose (Towbin, et al, Proc. Natl. Acad. Sci. 76, 1350, 1979). An immunoblot was performed using the 2B5 antibody as the primary antibody and $^{125}$I-goat anti-mouse affinity-purified antibody as the second antibody. As can be seen in FIG. 3, the 2B5 antibody recognizes kininogen antigen from normal plasma as two bands and kininogen antigen in HMWK-deficient plasma as one band. This finding indicates that the 2B5 antibody is directed to the heavy chain of HMWK, which is identical to the heavy chain of LMWK.

Figure 4:
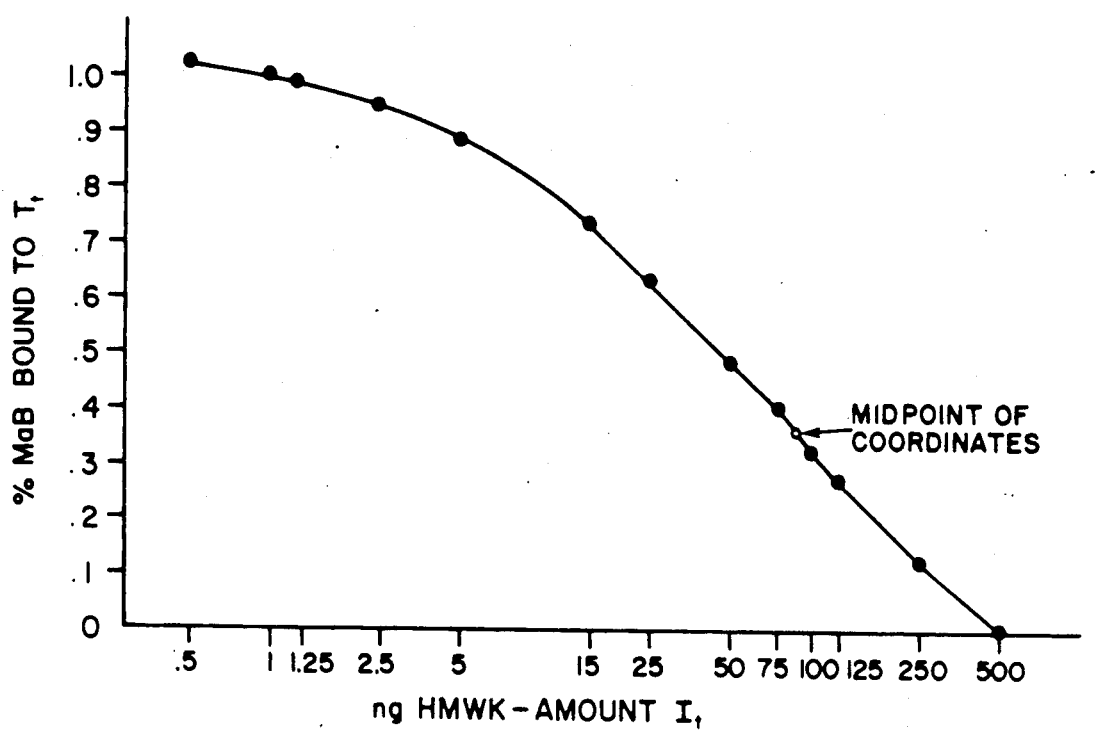
FIG. 4 is a plot of a four-parameter logistic function calculation of the competition inhibition of the 2B5 antibody by normal plasma.

The affinity of the 2B5 antibody for the HMWK heavy chain was studied further. Data from the competition inhibition of the 2B5 antibody by normal plasma was applied to a computer program to fit the curve by a four-parameter logistic function (Cannellas, P. F., Karu, A. E., J. Immunol. Meth. 47, 375, 1981) in order to determine the calculated midpoint of the curve (FIG. 4). This plot is also a standard curve for a quantitative CELISA. Using the calculated midpoint of the competition inhibition curve, the affinity of the antibody for antigen was determined by the formula of Muller (Meth. Enzymol. 92, 589, 1983), $K_a = 8/3(<I_t> - <T_t>)$. The calculated apparent $K_d$ of the antibody for antigen was 1.91 nM. This finding was confirmed by direct binding studies as follows.

Purified 2B5 antibody was radiolabeled with $^{125}$I by the Iodogen technique (Fraker, P. J., Speck, S. C. Biochem. Biophys. Res. Commun. 80, 849, 1978). Purified HMWK was linked to polystyrene cuvette wells. The radiolabeled antibody in the absence or presence of a fifty-fold molar excess of unlabeled antibody was incubated in the antigencoated cuvette wells. After subtracting non-specific binding from the Bound and Free portions, the slope of the line of Bound over Free versus Bound determines the affinity constant of the antibody for its antigen. Performing this study with the 2B5 antibody, the calculated apparent $K_d$ of this antibody for the heavy chain of the kininogen molecules was 1.76 nM.

Figures 5, 9:
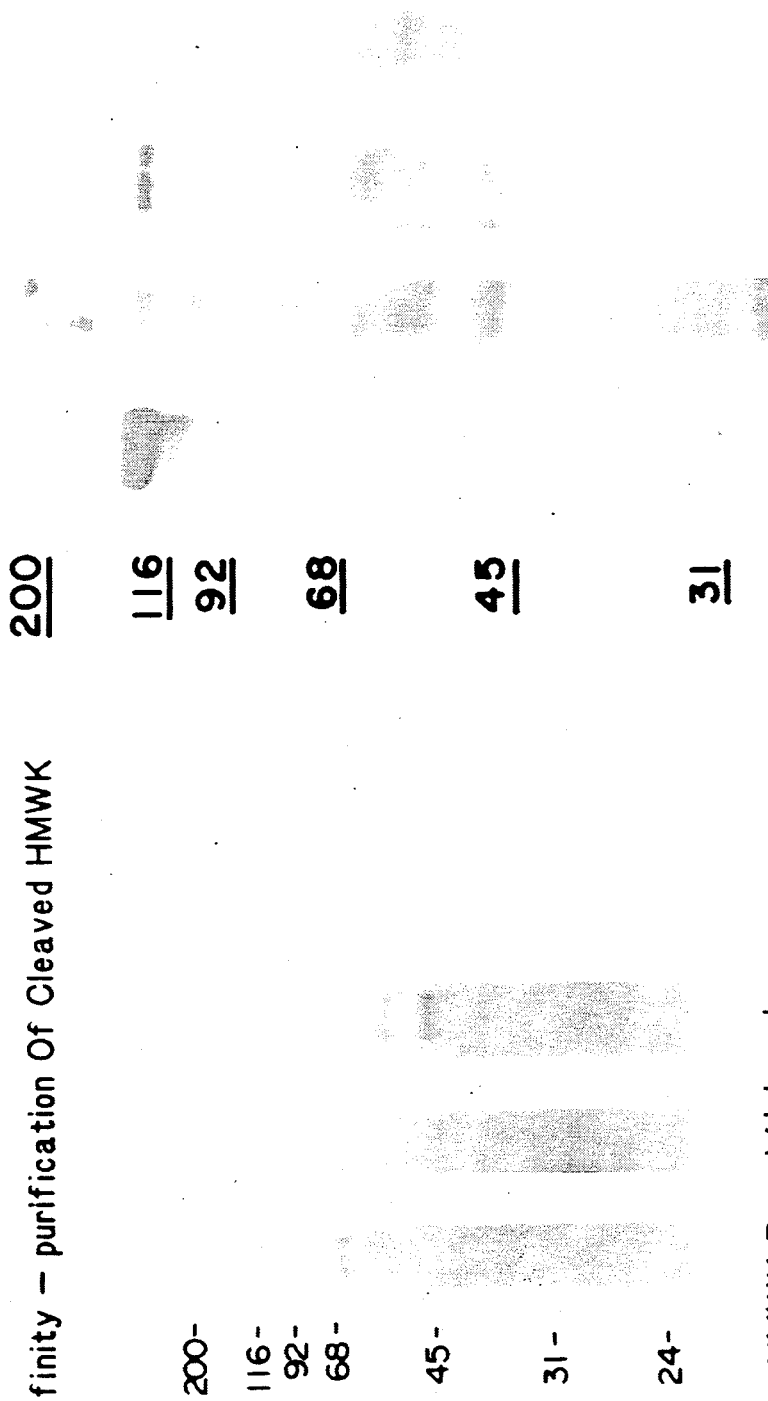
FIG. 5 is a sodium dodecyl sulfate polyacrylamide gel electrophoresis (SDS-PAGE) of purified, cleaved HMWK chains after alkylation and reduction. The lane marked "HMWK" represents purified HMWK. The lane marked "BOUND" represents HMWK heavy chain that is bound to an affinity column made from coupling the 2B5 antibody to cyanogen bromide-activated Sepharose 4B. The lane marked "UNBOUND" represents two forms of HMWK light chain that did not bind to the antibody attached to the support matrix.
FIG. 9 is a SDS-PAGE immunoblot using the CllCl antibody. The lane marked "HMWK" represents purified HMWK immunoprecipitated with the CllCl antibody. The "PLT LYS" lane indicates the immunoorecipitation of platelet high molecular weight kininogen with CllCl antibody. "HMWK PLT LYS" represents purified $^{125}$I-HMWK placed into a platelet lysate of total kininogen-deficient platelets and immunoprecipitated with the CllCl antibody. The "CN" lane represents a control immunoprecipitation from a platelet lysate using the CllCl antibody without the addition of Protein A.

Final characterization of the 2B5 antibody was performed by affinity chromatography (FIG. 5). Purified 2B5 antibody was linked to cyanogen bromide (CNBr)-activated Sepharose 4B (Meth. Enzymol. 82, 87, 1980). Purified HMWK was cleaved by purified plasma kallikrein (ratio kallikrein: kininogen = 1:130). The cleavage fragments were alkylated with iodoacetamide and reduced with dithiothreitol and applied to the 2B5 affinity column. As can be seen in FIG. 5, the two HMWK light chains (56 kDa, 46 kDa) did not bind to the column. However, the 64 kDa heavy chain did bind and had to be eluted with 4 M guanidine. On further testing of this affinity-purified material, only the unbound portion of the molecule contained the coagulant activity of HMWK. These combined studies indicate that the 2B5 antibody is directed to the heavy chain of the human plasma kininogen molecules.

Figure 6:
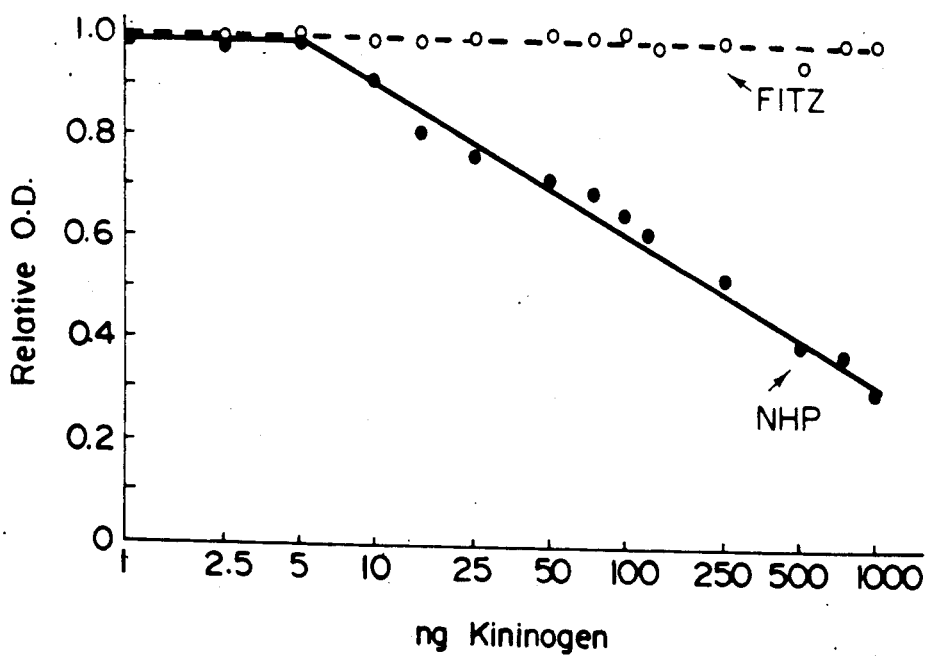
FIG. 6 is a plot of the competition inhibition of the CllCl antibody by kininogen antigen in normal plasma (NHP) and HMWK deficient plasma (FITZ).

Immunochemical studies were also performed on the CllCl antibody. Using CELISA, the CllCl antibody was consumed by kininogen antigen in normal plasma but not by kininogen antigen in HMWK-deficient plasma (FIG. 6). Not shown in the figure, total kininogen-deficient plasma did not consume the CllCl antibody. This finding suggests that the CllCl antibody is directed to the HMWK light chain since the only difference between the two plasmas was the presence of the light chain of the HMWK molecule in normal plasma.

The specificity of the CllCl antibody for the HMWK light chain was further tested on immunoblot studies. The antibody is similar to the 2B5 antibody in that it does not recognize antigen whose conformation may have been changed by the presence of sodium dodecyl sulfate. The same alkaline polyacrylamide gel electrophoresis, electroblotting and immunoblotting techniques as used for the 2B5 antibody (FIG. 3) were carried out with the CllCl antibody using normal plasma and HMWK-deficient plasma as a source of antigen. As can be seen in FIG. 7, the CllCl antibody recognized kininogen antigen in normal plasma but not kininogen antigen from HMWK-deficient plasma. This study confirms that the CllCl antibody is directed to the HMWK light chain.

Figure 8:
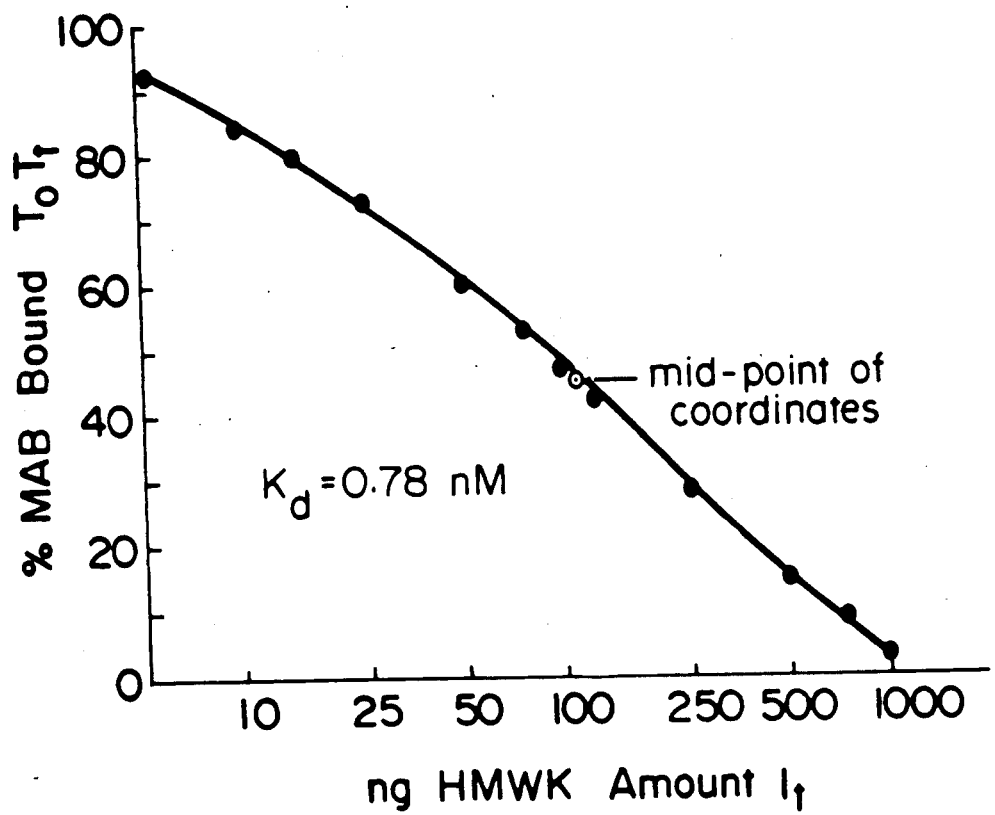
FIG. 8 is a plot of the four-parameter logistic function calculation of the competition inhibition of the CllCl antibody by normal plasma.

The affinity of the CllCl antibody for HMWK was studied by the same techniques employed for measuring the binding of the 2B5 antibody. Plotting the competition inhibition of the CllCl antibody by normal plasma on a fourparameter logistic function to determine its calculated midpoint of inhibition resulted in a calculated affinity of CllCl for its antigen of about $K_d=0.78$ nM (FIG. 8). This plot is also a standard curve for a quantitative CELISA.

VI. Functional Characteristics Of The Monoclonal Antibodies

Although the CllCl antibody neutralized the coagulant activity of HMWK, further studies were performed to determine if the 2B5 antibody influenced the activation of HMWK coagulant activity. Normal plasma was incubated with the 2B5 antibody overnight at 4°. Aliquots of the 2B5-treated normal plasma were compared with normal plasma alone to determine if it altered the activation of the HMWK coagulant activity. Normal plasma had peak HMWK activity when incubated with HMWK activating surface and phospholipid for nine minutes. 2B5-treated normal plasma exhibited a similar rate and extent of activation as normal plasma alone. This negative study indicates that the 2B5 molecule is directed to a portion on the HMWK heavy chain that in no way influences HMWK coagulant activity.

Further studies were performed to determine if 2B5 or CllCl recognize platelet high molecular weight kininogen. Using an immunoprecipitation technique with protein A, the CllCl antibody immunoprecipitated a form of platelet high molecular weight kininogen which was similar in size (120 kDa) to plasma and purified plasma high molecular weight kininogen (FIG. 9).

Additional studies were performed to determine if either the 2B5 or CllCl monoclonal antibody influenced the ability of the HMWK molecule to bind to its platelet receptor. In separate but simultaneous experiments the 2B5 or CllCl antibody independently almost completely inhibited exogenous $^{125}$I-HMWK binding to unstimulated platelets. This finding suggested that the HMWK molecule has two sites which are required for its association with the platelet surface.

VI. Quantitative Assay

The monoclonal antibodies of the present invention are useful in detecting changes in HMWK and LMWK concentrations in human plasma. The antibodies may be used to assay unknown samples of plasma for HMWK and total kininogen in a quantitative fashion by the following technique developed in our laboratory using a polyclonal antibody, Schmaier et al, J. Clin. Invest. 71, 1477 (1983).

A. Quantitative Assay Of HMWK With CllCl Antibody

Plasma concentrations of HMWK are determined by CELISA as follows. The CllCl monoclonal antibodies comprise the primary antisera and rabbit anti-mouse antibody conjugated with alkaline phosphatase is used as the secondary antibody. On day 1 100 ng of purified HMWK in 0.1 M $Na_2CO_3$ pH 9.6 is linked to the surface of polystrene cuvette wells (Gilford Instrument Laboratories Inc., Oberline, OH) by overnight incubation at 37° C. On the same day, incubation mixtures, in 1.5 ml conical polypropylene tubes (No. 72.690, Sarstedt, Inc., Princeton, N.J.) precoated with 0.2% bovine serum albumin, are made containing the following: 0.2 ml of antigen (purified HMWK or plasma solubilized platelets) diluted in 0.001 M sodium phosphate pH 7.4, 0.15 M NaCl containing 0.05% Tween-20 (PBS-Tween) and 0.2 ml of a 1:2500 dilution of CllCl antibody. These samples are then incubated overnight at 37° C. On day 2 each antigen-linked cuvette well is washed three times with PBS-Tween and incubated for 1 h at 37° C. with 0.2% radioimmunoassay grade bovine serum albumin. After washing, 0.2 ml from each incubation mixture is added to each cuvette well and incubated for 2 h at 37° C. At the conclusion of this incubation the rewashed wells are exposed to 0.2 ml of a 1:500 dilution in PBS-Tween of rabbit anti-mouse antibody conjugated with alkaline phosphatase. After another 2.5 h incubation at 37° C., the washed cuvettes receive sequentially timed additions of 0.4 ml of p-nitrophenylphosphate disodium (1 mg/ml) in 0.05 M $Na_2CO_3$, 1 mM $MgCl$, pH 9.8. At precise time intervals (10–20 min) after the addition of the substrate to each well, the amount of hydrolysis of the substrate in each well is either stopped with sequential additions of 0.4 ml of 2 M NaOH (final concentration 1 M NaOH) or was sequentially measured spectrophotometrically in a PR50 EIA Processor-Reader (Gilford Instrument Laboratories, Inc.) at 405 nm.

The CELISA assay is standardized against purified HMWK. Purified single-band HMWK is diluted according to its protein concentration determined by protein assays. Protein assay may be according to the method of Lowry et al., J. Biol. Chem. 193, 265-275 (1951) or Bradford, Anal. Biochem. 72, 248 (1976), for example. The amount of HMWK antigen in one pool of normal human plasma (lot No. NIO George King, Biomedical, Inc.) is compared with the purified HMWK diluted in total kininogen-deficient plasma on electroimmunodifusion using polyclonal anti-HMWK antisera. All subsequent dilutions of pooled normal plasma are based on the amount of HMWK antigen determined in the pool. Samples for the standard curve (purified HMWK, plasma) and unknowns (plasma) are both assayed at 10 different dilutions in triplicate. All data are analyzed on a TRS-80 model III computer (Tandy Corp., Forth Worth, Tex.). Raw optical density readings are averaged after the blanks are substracted. Outliers are defined as points with a greater than 10% SD. A best-fit standard curve is determined by nonlinear regression. The best-fit standard curve is then entered into an iterative computer program that uses a four-parameter logistic function and an optional weighting function for a sigmoidal line fit of the standard curve. Canellas, et al, J. Immunol. Methods 47, 375-385 (1981). The weighting function is determined by a multiple linear regression for each batch of antisera. Id. This program yields a semilogarithmic graph (FIG. 8) in which the ordinate is the optical absorbance calculated in relative values from 0 to 1 and the abscissa is the absolute amount of antigen incubated with antisera. Unknown plasma samples are determined by linear least squares regression from the standard curve of the iterative program and the calculated slope of the regression line is an estimate of the specific activity of the sample. Test sample determinations that are considered valid are computed results that fall on the linear portion of the standard curve for the individual assay and are characterized by a regression analysis having p values less than 0.05 in an F test on the determination of the line and in a t test against the null hypothesis that the slop of the line equals zero. The C11C1 antibody may thus be used to quantitatively assay unknown samples for HMWK content.

B. Quantitative Assay of Total Kininogen/LMWK With 2B5 Antibody.

The above assay procedure, repeated with the 2B5 antibody, provides a quantitative assay for total kininogen content. The data, when analyzed and plotted in accordance with the above-described four-parameter logistic function, results in the curve shown in FIG. 4, which may be used to assay unknown samples for total kininogen content. Subtracting the HMWK content of a plasma as measured by the C11C1 antibody from the plasma's total kininogen content as measured by the 2B5 antibody indicates the LMWK concentration in the plasma.

The antibodies may thus be used to diagnose activation of the contact coagulation system, which can be signalled by changes in the levels of the plasma kininogens.

Detection and quantitation of kininogen in any specimen of interest can be carried out with the present monoclonal antibodies using a CELISA or a radioimmunoassay. Techniques have already been developed to radiolabel these antibodies. As indicated in the CELISA experiments which led to FIGS. 2, 4, 6 and 8, the antibodies are incubated with the specimen, and the material bound thereto is measured indirectly by the amount of enzyme-absorbed secondary antibody bound to a cuvette well. Other quantitative immunological assays may be used, including, but not limited to CELISA, radioimmunoassay, ELISA, fluorescent-antibody assay, precipitation, agglutination, and electroimmunodiffusion. Such methods also include fast liquid chromatographic methods such as ion exchange, gel filtration and reverse phase chromatography.

The present monoclonal antibodies are thus useful to measure kininogen levels in the plasma in pathogenic states related to the contact activation of the coagulation pathway. These pathogenic states include, but are not limited to, acquired disorders such as gram negative or positive sepsis, peridontal disease, carcinoid syndrome, postgastrectomy syndrome, nephrotic syndrome, type IIa hyperlipoproteinemia, allograft rejection, allergic reactions, typhoid fever, viremia, and Rocky Mountain Spotted Fever. The monoclonal antibodies are also useful in measuring abnormal kininogen levels connected with hereditary disorders such as hereditary angioedema.

Apart from plasma, other specimens of interest include saliva, nasal secretions, platelets, kidney, urine, leukocytes, skin, heart, liver and endothelial cells.

Since the C11C1 antibody is specific for HMWK and does not bind LMWK, while the 2B5 antibody binds both LMWK and HMWK, the antibodies may be used in serial fashion to determine the level of HMWK and LMWK in the same sample.

The monoclonal antibodies of the present invention are also useful in removing high and low molecular weight HMWK and LMWK from the blood or any body fluid or suspension, thereby providing a method of therapy for any possible (but not yet demonstrated) disease condition wherein the patient may suffer from increased levels of these proteins. Following removal of excessive amounts of these proteins from blood, the tissue may be returned to the body.

A method for purifying human plasma kininogen is provided. The monoclonal antibodies of the present invention may be easily covalently bound to an immobilized matrix such as CNBr-activated Sepharose, as disclosed above. Both plasma kininogens may be purified by passing plasma through such a column containing immobilized monoclonal antibody, and then eluting the bound kininogen. Purification of the kininogens in this manner may take place with or without prior partial purification, such as by ion exchange chromatography.

A column of the type described above may also be used to separate the light and heavy HMWK chains since the two antibodies of the present invention are specific for different epitopes on the light and heavy chains. Moreover, the heavy chain-directed antibody 2B5 can be used to purify LMWK directly from plasma. Finally, because HMWK binds prekallikrein and factor XI, columns of this type charged with HMWK may be used to purify these proteins.

The hybridomas of the present invention secrete antibody belonging to sub-class $IgG_1$, which means the antibodies have the same "constant" region. An antibody to a specific antigen has a constant region and a "variable" The variable region recognizes antigen, regardless of the type of constant region. Thus, monoclonal antibodies exhibiting the characteristics described herein may be of sub-class $IgG_1$, $IgG_{2a}$, $IgG_3$, IgM, IgA or other Ig classes. Since the difference in immunoglobulin class (Ig) will not effect the pattern of reactivity of the antibody toward the antigen, it is contemplated that all monoclonal antibodies to human kininogen are included within the subject invention regardless of Ig class or sub-class.

The method of the present invention for preparing monoclonal antibodies to human kininogen, which includes immunization, fusion and selection of hybridomas, may be followed to generate cell lines other than the two cell lines disclosed herein. Because individual hybridomas may be identified only by the antibody which they produce, it is contemplated that any hybridoma-producing antibody to any human kininogen is included within the scope of the present invention, as are methods for making such antibodies employing hybridomas. It is further contemplated that splenocytes and myelomas from other vertebrates, such as human, rat, bovine, porcine, etc., not just those of murine origin, may be used to form hybridomas using the methods described herein.

The monoclonal antibodies of the present invention are produced by hybridomas. However, it is contemplated that other methods of cell-immortalization may be used to produce monoclonal antibodies against human kininogen. These methods are known to those skilled in the art. For example, human antibody-producing lymphocytes may be immortalized by transformation with Epstein-Barr virus. See, e.g., Chiorazzi, et al, J. Exp. Med. 56, 930–35 (1982); Steintz, et al, J. Immunol. 132, 877–82 (1984).

The present invention may be embodied in other specific forms without departing from the spirit or essential attributes thereof and, accordingly, reference should be made to the appended claims, rather than the foregoing specification, as indicating the scope of the invention.

What is claimed:

1. A method for determining the level of human kininogen in a specimen comprising contacting the specimen with a monoclonal antibody which binds to an antigenic determinant of human kininogen, and measuring the human kininogen bound by said antibody by an assay means, which antigenic determinant is characterized by binding to monoclonal antibody produced by hybridoma ATCC #HB-8963 or ATCC #HB-8964.

2. A method according to claim 1 wherein the specimen is selected from the group consisting of plasma, saliva, nasal secretions, platelets, kidney, urine, skin, leukocytes, heart, liver, and endothelial cell.

3. A diagnostic method according to claim 2 wherein the monoclonal antibody is produced by a hybridoma selected from the group of the hybridomas numbered ATCC #HB-8963 and ATCC #HB-8964.

4. A diagnostic method according to claim 1 wherein said assay means is an immunological assay means selected from the group consisting of radioimmunoassay, enzyme-linked immunosorbent assay, CELISA, fluorescent assay, radial immunodiffusion, precioitation, electroimmunodiffusion, and agglutination.

5. A diagnostic method according to claim 1 wherein the assay means is fast liquid chromatography.

* * * * *